United States Patent [19]

Barkan

[11] 4,191,189
[45] Mar. 4, 1980

[54] STONE DISINTEGRATOR

[76] Inventor: Yale Barkan, 835 Amigos Way, No. 17, Newport Beach, Calif. 92660

[21] Appl. No.: 843,402

[22] Filed: Oct. 19, 1977

[51] Int. Cl.² ............................................. A61B 17/00
[52] U.S. Cl. .................................... 128/328; 128/421
[58] Field of Search ............. 128/328, 419 PG, 419 P, 128/419 S, 419 B, 419 D, 421, 423, 2 P, 1 R, 303 R, 422, 303.14

[56] References Cited

U.S. PATENT DOCUMENTS

| | | | |
|---|---|---|---|
| 2,294,411 | 9/1942 | Lag | 128/423 |
| 2,764,683 | 9/1956 | Pavst et al. | 128/423 |
| 2,823,678 | 2/1958 | Luftman et al. | 128/422 |
| 3,699,389 | 10/1972 | Holsinger | 128/2.1 P |
| 3,794,841 | 2/1974 | Cosentino et al. | 128/2.1 P |
| 3,902,499 | 9/1975 | Shene | 128/328 |
| 4,027,674 | 6/1977 | Tessler et al. | 128/328 |
| 4,123,673 | 10/1978 | Gonser | 128/303.14 |

OTHER PUBLICATIONS

*Basic Electronics for Engineers & Scientists*, by Russell E. Lueg and Erwin A. Reinhard, Intext Educational Pub., 1972.

*Primary Examiner*—Robert W. Michell
*Assistant Examiner*—C. W. Shedd
*Attorney, Agent, or Firm*—Kane, Dalsimer, Kane, Sullivan and Kurucz

[57] ABSTRACT

An instrument for disintegrating calculi in the urinary tract by hydraulic impacts formed by electrical discharges in the liquid medium surrounding the calculi wherein the electrical discharges are provided by a spark discharge circuit employing a high voltage, vacuum type or gas filled relay controlled by a pulse generator. Capacitors charge lithotrites to form the electrical discharge. The capacitors are discharged through circuits employing the high voltage relay. Specifically, the relay switches the lithotriptor electrodes directly across a charged capacitor thereby producing a spark discharge across the electrodes. The spark discharge repetition rate and its intensity are controlled by circuit parameters.

7 Claims, 4 Drawing Figures

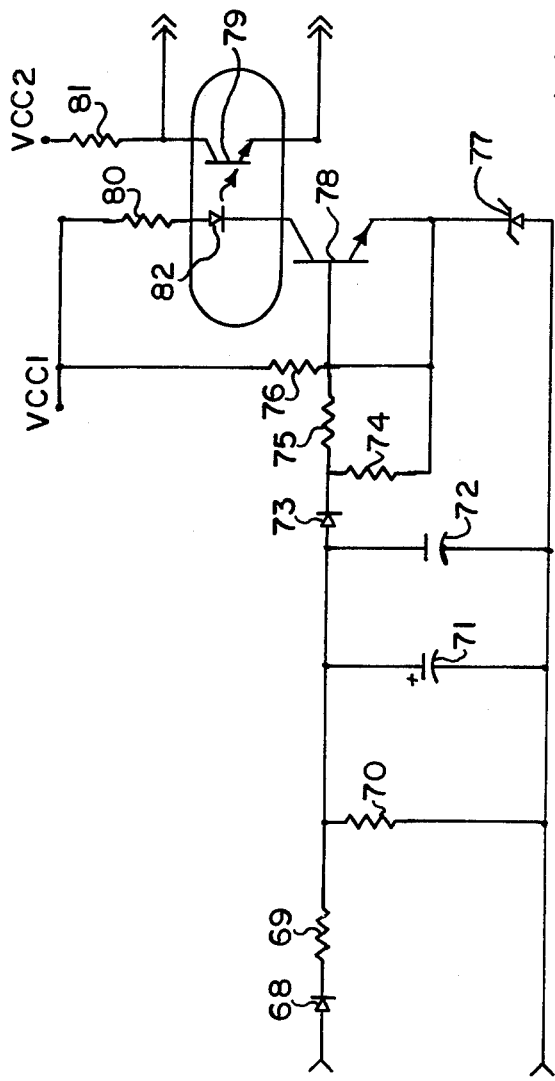
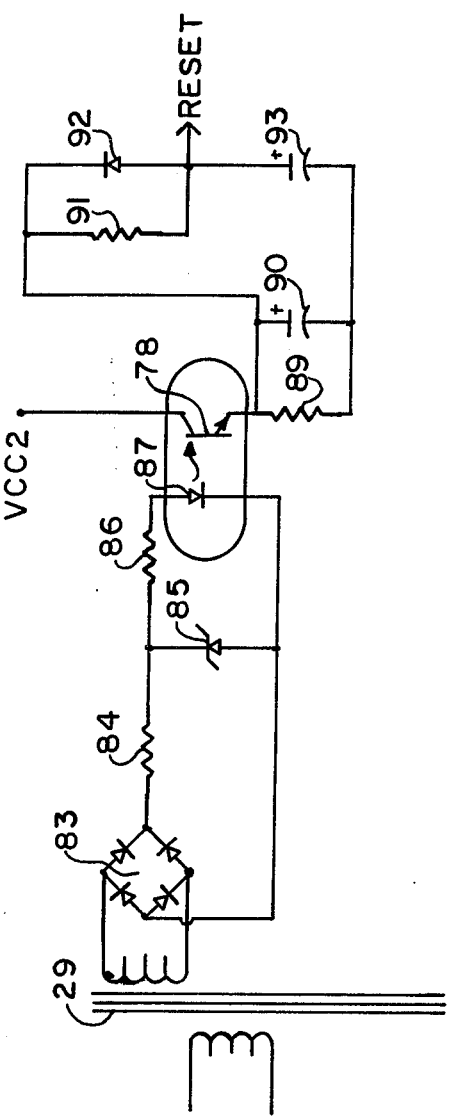
FIG. 3
STANDARD INPUT CIRCUIT (S.I.C)
FIG. 4
INITIALIZATION CIRCUIT

STONE DISINTEGRATOR

BACKGROUND OF THE INVENTION

It is known in the prior art to use hydraulic impacts due to electrical discharge to disintegrate calculi in the urinary tract as is shown in U.S. Pat. No. 3,902,499. The prior art as taught in U.S. Pat. No. 3,902,499 employes solid state switches known generally as thyristors in the spark discharge circuits. It is commonly known that thyristors have disadvantages. Only limited values of voltage can be applied from anode to cathode in the device "off state" without destruction of the device. In order to obtain sufficient voltage to discharge the lithotrite electrodes with sufficient energy to fragment bladder calculi the thyristors have to be connected in a series arrangement of three or more devices so that the voltage across each thyristor is within its rating. With series arrangements of thyristors a critical timing requirement exists on the gate trigger signals in order to provide simultaneous turn on of all the thyristors. Application of gate signals with wave fronts less than 1 microsecond apart are required. If all the thyristors do not turn on simultaneously one or more of the devices will experience an anode to cathode voltage beyond its maximum rating causing destruction of the device or devices, as the case may be. Even with the gate signal requirement met, variations in the turn-on characteristics between individual thyristors preclude simultaneous turn-on of all thyristors in a series arrangement thereby seriously reducing the reliability of such a circuit configuration or its practicability.

Another disadvantage of the use of thyristors in such equipment is that the cost is high for each device that meets the high voltage, high current requirements of the instrument described. Use of more than one thyristor in a series arrangement further increases the instrument cost.

A further disadvantage in the use of thyristors pertains to the use of a pulse generator as taught in the prior art U.S. Pat. No. 3,902,499 having means of varying the pulse duration of the pulses applied to the thyristor gates thereby controlling the interval the capacitors will be discharged through the thyristors when the thyristors are in the "on state". Varying pulse width is a disadvantage in that the "on state" interval of thyristor is not controllable by the duration of the gate signal. In these thyristors the initiation of the "on state" does indeed occur with application of the gate signal but termination of the "on state" requires the removal of the anode voltage to a level below that value necessary to sustain the minimum holding current of the device.

SUMMARY OF THE INVENTION

In order to overcome the disadvantages of the instruments known in the art an instrument is provided wherein the spark discharge circuit employes a high voltage gas filled or vacuum type relay. Specifically, the relay switches the lithotriptor electrodes directly across a charged capacitor thereby producing a spark discharge.

The relay is controlled by a pulse generator with a selectable pulse repetition rate. The total number of pulses in each burst is selectable by push-button switches on a panel. Each burst is initiated by activation of a foot switch.

The repetition rate of the lithotrite discharge is directed by the generator. The intensity of the discharge is established by the amount of energy transferred to the lithotrite from the charged capacitor and the time duration of the discharge. The amount of energy is established by the initial charged capacitor voltage and the value of capacitors. The spark discharge duration is primarily established by the voltage discharge time constant. Means are provided to select the amount of energy in each spark discharge.

BRIEF DESCRIPTION OF THE DRAWINGS

In the drawing:

FIG. 3 is a schematic of the input circuit; and

FIG. 4 is a schematic of the initialization circuit.

DESCRIPTION OF THE PREFERRED EMBODIMENT

Figure 1:
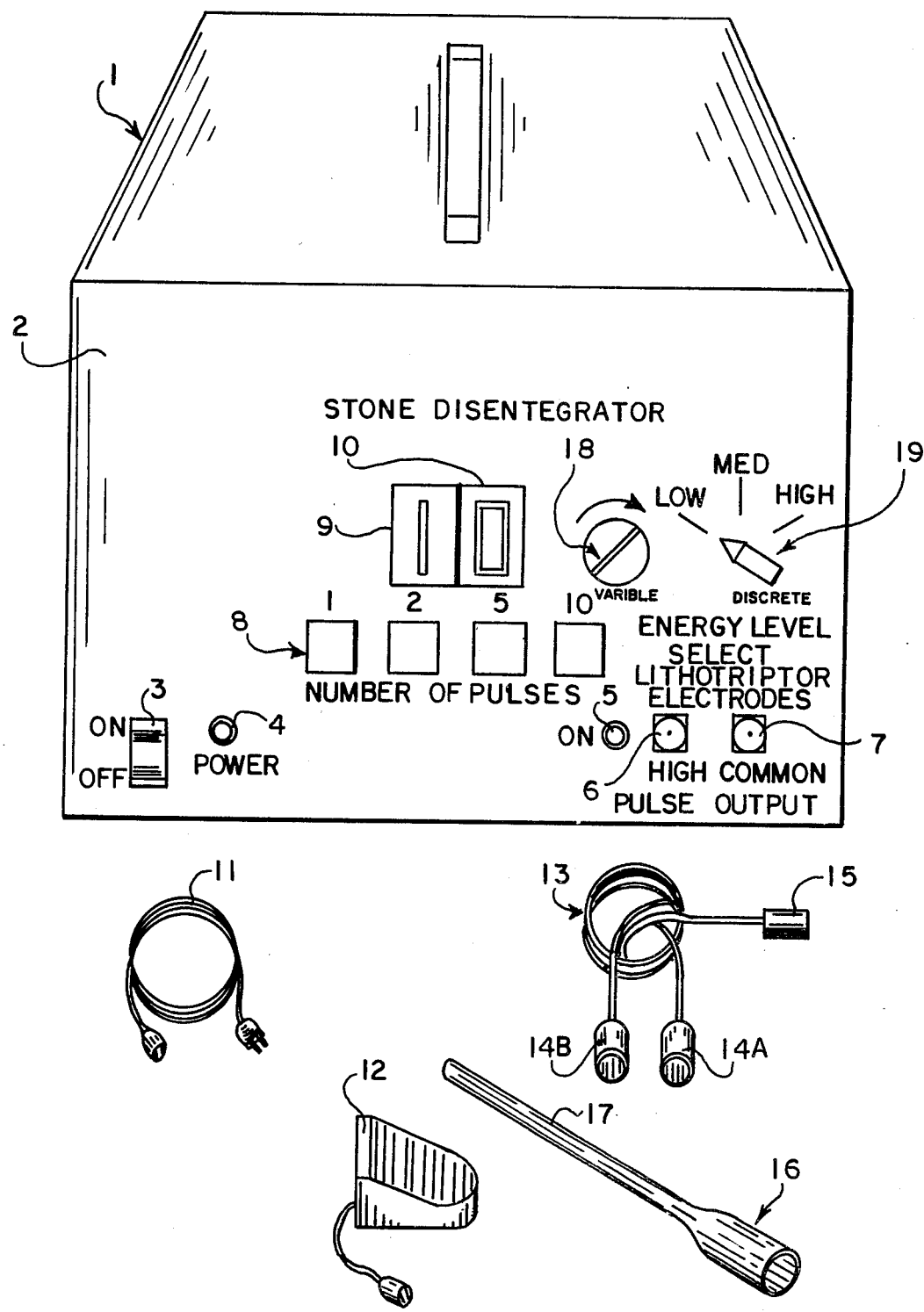
FIG. 1 is a perspective view from the front of an instrument constructed in accordance with the teachings of this invention with certain of the peripheral components shown associated therewith.

As shown in the figures, the instrument is designated by the numeral 1. The front panel 2 includes power on-off switch 3, power indicator lamp 4, pulse indicator lamp 5 which is on for the duration of each pulse applied to the high voltage vacuum relay, high voltage connector 6 and high voltage connector 7. Connector 6 connects the upper contact arm of the voltage vacuum relay to the inner electrode connection of the lithotriptor electrode connector, and connector 7 connects the remaining or lower relay contact arm to the coaxial outer electrode connection of the lithotriptor electrode connector. The lithotriptor electrode connector in the Figures is designated by the numeral 16.

Push button 8 is provided to select the total number of pulses in each burst and indicator 9 displays the 10s digit of the digital display indicating the total number of pulses selected by push button 8 while indicator 10 displays the ones digit. The numerals 11, 12 and 13 identify the power cord, foot switch and lithotriptor cable respectively. Activation of the foot switch initiates the pulse train that drives the high voltage relay and the cable 13 provides the connection of the lithotrite 17 with connector 16 to the cable connector 15. The inner electrode of the lithotrite 17 is connected through connector 16 to connector 15 through the cable to connector 14a and is hence connected to connector 6 on the front panel. The outer coaxial electrode of the lithotrite 17 is connected to the outer connector electrode of connection 16 and to the outer electrode of connector 15 through the cable to connector 14b and is thence connected to connector 7 on the front panel.

Figure 2:
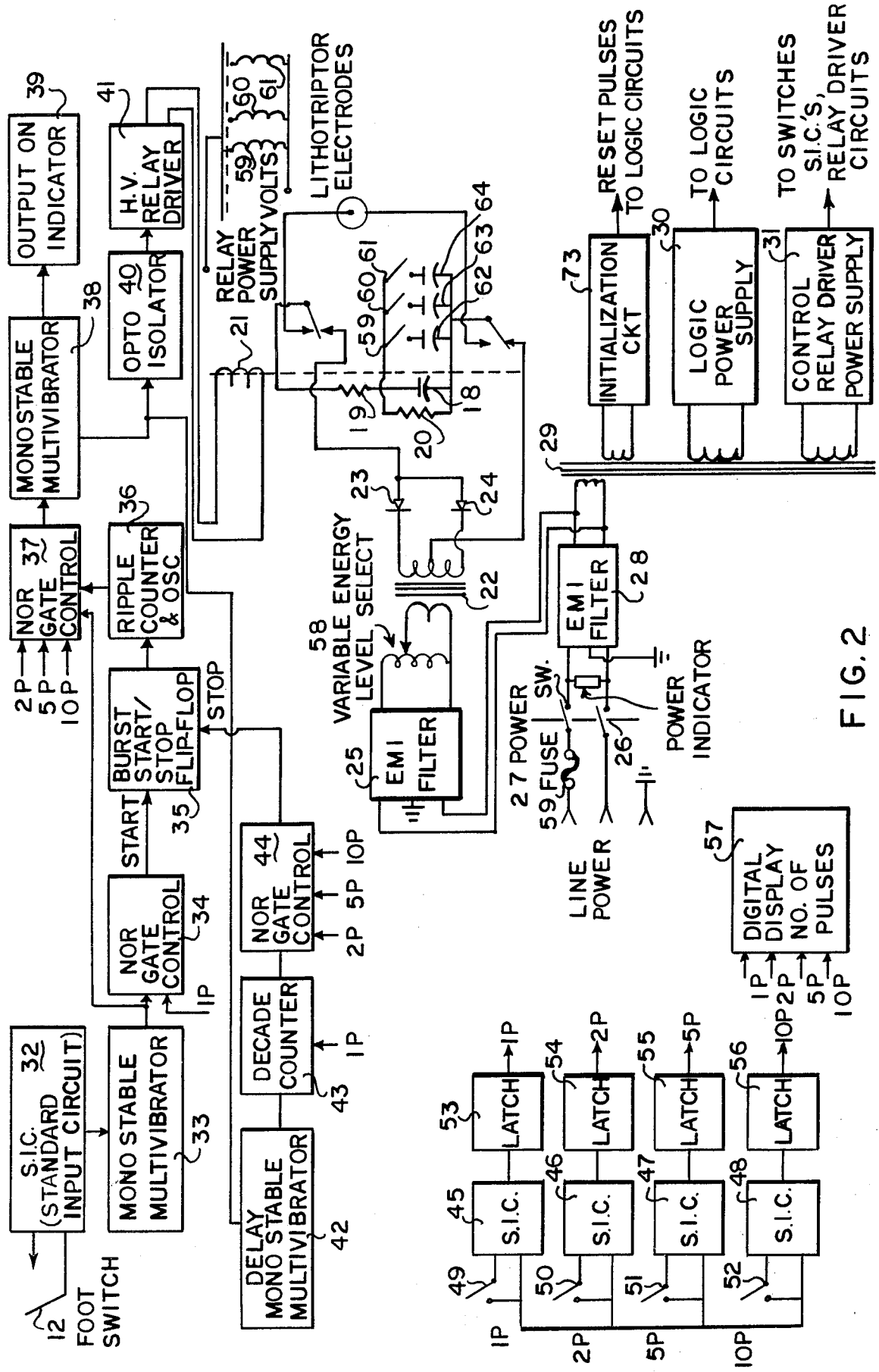
FIG. 2 is a system block diagram in schematic form of the circuit for operating and controlling the instrument.

The instrument provides a means of precise control of a selectable number of lithotriptor discharge pulses, the energy content, and discharge pulse duration being constant and repeatable. This control is accomplished in the high voltage gas filled or vacuum type relay 21, a variable input voltage to the pulse transformer as provided by autotransformer 58, and discrete values of capacitance as provided by relays 59, 60 and 61 and capacitors 18, 62, 63 and 64, as shown in FIG. 2. Since the energy stored in a capacitor is equal to $\frac{1}{2}CV^2$ (Where C equals capacitance and V the voltage across the capacitance) means are provided by autotransformer 58 to control the voltage across the capacitors and relays 59, 60 and 61 are used to establish the total amount of capacitance connected in the circuit.

The high voltage power supply consists of an EMI filter 25, autotransformer 58, a step-up pulse transformer 22, high voltage rectifier diodes 23 and 24, energy storage capacitors 18, 62, 63 and 64, bleeder resistor 20, series resistor 19 and switching high voltage relays 59, 60 and 61. The capacitors 18, 62, 63 and 64 charge up to the peak value at the full wave rectified voltage in a few cycles of the input power supply frequency. A DPDT high voltage gas filled or vacuum type relay 21 switches the lithotriptor electrodes 17 directly across the charged capacitors.

Since the initial voltage across the charged capacitor exceeds the breakdown voltage established by the electrodes gap distance and the breakdown characteristic of the medium in which the lithotriptor electrodes are submerged, a spark discharge occurs. The duration of the discharge is primarily controlled by the discharge time constant of the capacitors 18, 62, 63 and 64 series resistor 19 and the low impedance of the arc. The relay 21 is kept energized for a sufficient time interval so that the capacitor is essentially fully discharged and the arc is extinguished.

Upon termination of the relay driver pulse, the relay deenergizes and removes the lithotriptor electrodes from the energy storage capacitor. The capacitor charges up to the power supply voltage and the operation sequence repeats when the relay is energized by the next driver pulse.

In addition to performing the energy switching function in a controlled, repeatable manner, another advantage of the relay is that it provides essentially complete electrical isolation of the lithotrite and the patient from the instrument during the relay deenergized state. A high degree of isolation and negligible shock hazard is also provided during the discharge interval since there are no direct external connections from the secondary of the pulse transformer 22 to the instrument case. A low leakage EMI filter 25 provides isolation of the transformer and power supply circuits that generate EMI from the line power and the low voltage power supplies 30 and 31. The bleeder resistor 20 provides the safety of discharging the capacitor 18 when the instrument is turned off by power switch 26 or power is interrupted to the instrument by any other means. Momentary actuation of the foot switch 12 produces a pulse that either actuates the relay directly, in the single pulse mode or activates a Burst start/stop flip-flop 35 in the multi-pulse mode operation. The flip-flop starts an oscillator and ripple counter 36. The output of the counter changes state with selectable time intervals and triggers a mono stable multivibrator 38 that provides pulses of uniform duration and recurrance times. These pulses are optically coupled 40 to a relay driver 41 that actuates the relay 21, that switches the lithotropter electrodes 17 directly across the charged capacitor 18. Simultaneously, these pulses are fed into a delay multivibrator 42 and thence to a decade counter 43. The decade counter is deactivated in the single pulse mode. In multi-pulse operation, the counter counts the pulses that drive the relay 21 and stops the oscillator and ripple counter via the Burst start/stop flip-flop at the number of pulses determined by the selected mode.

As an example, in the five pulse mode of operation, the initial pulse generated from activation of the foot switch and four pulses from the ripple counter are combined in the NOR gate control circuit 37 to provide a five pulse burst with a pulse repetition interval of 50 milliseconds. The number of pulses in a burst is selected by Front panel mounted switches 49, 50, 51 or 52. In the preferred embodiment, selection of 1, 2, 5 and 10 pulses can be made with a pulse repetition time of 35 milliseconds. The number of pulses and pulse repetition time are not limited to these values.

Only momentary actuation of these switches is required since flip-flop type latches 53, 54, 55 and 56 are used to retain actuation information, and the latch outputs are used throughout the instrument as steering signals to provide proper mode operation. The latch outputs are also used as inputs to the display circuits 57 that displays the selected mode in a ten's and one's digital display format.

Proper operation of the logic control circuits in the presence of electrical noise from any source outside the instrument and inherent switch contact bounce is accomplished by a standard input circuit (SIC) located between the foot switch and the mode switches and the inputs to the logic circuits (circuits 32, 45, 46, 47 and 48).

The standard input circuits contain elements to provide (a) transmission of unipolar control signals via diodes 68 and 73, (b) filtering with the combination of elements 69, 70, 71 and 72, (c) noise immunity against noise levels of several volts by zener diode 77, and (d) optical isolation of the switches and SIC input circuits from the logic input circuits by the opto-isolator 79. These isolators provide isolation from unwanted direct and alternating voltage with magnitudes of hundreds of volts. A switch closure presents a positive voltage at the input to the circuit. This voltage is passed by the input diode 68 and filtered by the network elements 69, 70, 71 and 72. The filtered signal is passed by diode 73, and switches transistor 78 to its "on-state". Resistors 74 and 75 provide proper base drive and return. The signal level to the transistor base must be greater than a threshold value established by zener diode 77, in the emitter circuit of transistor 78. The zener voltage in combination with the chosen switch voltages establish a noise immunity threshold of several volts. Resistor 76 establishes the zener diode operating point.

When transistor 78 switches on, collector current through the opto-isolation diode 82, and limited by resistor 80, switches the opto-isolator transistor 79 to its "on-state"; thereby producing the desired change in voltage level sensed by the logic circuits. Collector current of output transistor 79 is limited by resistor 81. Diodes 68 and 73 prevent negative noise excursions from affecting circuits operation.

Electromagnetic radiation interference is produced by the current pulses in the connecting wires of the energy storage capacitor 18, high voltage relay 21 and lithotropic electrodes 17 during the energy discharge into the arc across the electrodes gap. Current magnitudes of hundreds of amperes for several microseconds and contact bounce of the relay contacts produce radiation interference over a wide frequency range from several kilohertz to several megahertz.

This interference (EMI) is prevented from affecting the operation of the instrument by careful design of the mechanical package using rules well known to those skilled in the art. EMI filters 25 and 28 prevent EMI from entering the supply power lines, the logic and control power supply circuits 30 and 31.

An initialization circuit 83 provides proper operation of the instrument when it is turned on or off by power switch 26, or when power is interrupted to the instrument for any reason. The circuit operates from a full wave rectified voltage derived from a secondary winding of the transformer 29 and full wave rectifier 83. The circuit provides the reset pulses for all the logic control circuits. The network consisting of elements 84 and 85 limit the magnitude of the full wave rectified voltage that is applied to the opto-isolator diode 87, through resistor 86. The diode is switched on during most of each half cycle of the input but turns off during the portion of the waveform that approaches zero volts during each half cycle. This negative going voltage spike is filtered by the network composed of resistor 89 and capacitor 90. The time constant of this network is sufficiently short so that normal operation of the circuit is not affected. Thus, a positive supply voltage is available to the network comprised of resistor 91, diode 92 and capacitor 93, when the power switch 26 is turned on. The voltage at the plus side of capacitor 93 rises with a time constant established by the product of resistor 91 and capacitor 93. This time constant is significantly greater than the time required for the logic power supply voltage from supply 30 to reach its operating level. Thus, the reset pulse applied to the logic circuits provides correct initialization of these circuits. When the power switch 26 is turned off, the capacitor 93 discharge through diode 92 and resistor 89. This time constant is much shorter than the decay characteristic of the logic power supply 30. Thus, the logic circuits are kept in a reset condition by the low voltage level at the plus side of capacitor 93 during shut down. This operation prevents extraneous lithotriptor discharge pulses from occuring during shut down when the power switch is turned off or shut down by other means occurs, such as a facility power failure.

In operation the lithotrite is inserted in the urinary bladder, which is filled with washing fluid. The lithotrite is then visually manipulated until the top of the lithotrite is in contact with the calculus. Power will have been turned on beforehand, so that it will merely be necessary for the operator to step on foot pedal switch to initiate an electrical discharge in the fluid medium surrounding the calculus.

If the calculus is hard, smooth, or large, the magnitude of the total discharge energy will be made high by selecting a larger number of pulses in each burst with the control on the front panel of the instrument. Repeated electrical discharge bursts are applied until the calculus is so disintegrated that it can be removed by flushing.

I claim:

1. An instrument for disintegrating calculi in the urinary tract by hydraulic impacts formed by electrical discharges in the liquid medium surrounding the calculi including in combination a lithotrite for providing said electrical discharges, first and second spaced lithotriptor electrodes of said lithotrite, capacitor means, a high voltage relay for selectively connecting and disconnecting said lithotriptor electrodes across said capacitor means; and when said relay has disconnected said lithotriptor electrodes, said electrodes are electrically isolated from the capacitor means; means for charging said capacitor means, including rectifying and filtering means, and control means for said relay, said contol means including a pulse generator of selectable pulse repetition rate, and input circuit means to said pulse generator including unipolar initiation signal transmission means, and isolation and threshold filtering means.

2. An instrument in accordance with claim 1 in which said relay provides electrical isolation of the lithotrite from said control means when deenergized, said means for charging said capacitor means is electrically isolated by said filtering means and a bleeder resistor is provided operatively associated with said capacitor means for discharging said capacitor means to ground upon discontinuance of power to said instrument.

3. An instrument in accordance with claim 1 in which said high voltage relay is a gas filled relay.

4. An instrument in accordance with claim 1 in which said high voltage relay is a vacuum type relay.

5. An instrument in accordance with claim 1 in which means are provided for discrete selection of energy level in the electrical discharge, said means including switching means for introducing and removing capacitors in said circuit.

6. An instrument in accordance with claim 1 in which said control means further includes an autotransformer input to said pulse transformer, said autotransformer being provided with variable energy level selection means.

7. An instrument in accordance with claim 1 including logic circuit means and a logic power supply for said logic circuit means and said initiation signal transmission means includes a full wave rectifier, isolator diode means, magnitude limiting means to limit the magnitude of the full wave rectified voltage from said fullwave rectifier and apply it to said isolator diode means whereby said isolator diode is switched on during the major portion of each half cycle and turns off during the portion of each half cycle that the wave form approaches zero, a filter network receiving the output from said isolator diode and load means including a load capacitor and load diode whereby a positive supply voltage is available to said load means when power is turned on and the voltage at the plus side of said load capacitor rises and when power is turned off said load capacitor discharges through said load diode; the time constant of charging said load capacitor is greater than the time required for said logic power supply to reach the operating level upon turn on and the time constant of discharging said load capacitor is lower than the decay characteristic of said logic power supply upon power turnoff.

* * * * *